US008639678B2

(12) United States Patent
Somasundaran et al.

(10) Patent No.: US 8,639,678 B2
(45) Date of Patent: Jan. 28, 2014

(54) SYSTEM FOR GENERATING A MEDICAL KNOWLEDGE BASE

(75) Inventors: Swapna Somasundaran, Lawrenceville, NJ (US); Vinodkumar Prabhakaran, Bronx, NY (US); Vinay Damodar Shet, Princeton, NJ (US); Kateryna Tymoshenko, Trent (IT); Mathäus Dejori, New York City, NY (US)

(73) Assignee: Siemens Corporation, Iselin, NJ (US)

( * ) Notice: Subject to any disclaimer, the term of this patent is extended or adjusted under 35 U.S.C. 154(b) by 0 days.

(21) Appl. No.: 13/479,363

(22) Filed: May 24, 2012

(65) Prior Publication Data

US 2013/0066870 A1  Mar. 14, 2013

Related U.S. Application Data

(60) Provisional application No. 61/533,412, filed on Sep. 12, 2011, provisional application No. 61/602,636, filed on Feb. 24, 2012.

(51) Int. Cl.
*G06F 17/30* (2006.01)

(52) U.S. Cl.
USPC .......................................... 707/705; 707/706

(58) Field of Classification Search
USPC ................................. 707/705, 706
See application file for complete search history.

(56) References Cited

U.S. PATENT DOCUMENTS

2006/0047649 A1* 3/2006 Liang ................................. 707/4
2006/0106793 A1* 5/2006 Liang ................................. 707/5

OTHER PUBLICATIONS

Cartic Ramakrishnan, et al., "A Framework for Schema-Driven Relationship Discovery from Unstructured Text", The Semantic Web—ISC 2006, pp. 583-596, 2006.
Asma Ben Abacha and Pierre Zweigenbaum, "A Hybrid Approach for the Extraction of Semantic Relations from MEDLINE Abstracts", In Proceedings of the 12th international conference on Computational linguistics and intelligent text processing—vol. Part II, pp. 139-150. Springer-Verlag, 2011.
Asma Ben Abacha and Pierre Zweigenbaum, "Automatic extraction of semantic relations between medical entities: a rule based approach", Journal of Biomedical Semantics, 2(Suppl 5): S4, 2011.
B. Rosario and M.A. Hearst, "Classifying semantic relations in bioscience texts". In Proceedings of the 42nd annual meeting on association for computational lin-guistics, pp. 430-es. Association for Computational Linguistics, 2004.

(Continued)

*Primary Examiner* — Baoquoc N To
(74) *Attorney, Agent, or Firm* — Joshua B Ryan

(57) ABSTRACT

A system generates medical knowledge base information by searching at least one repository of medical information to identify sentences including a received medical term. A data processor searches the identified sentences to identify sentences including a medical term different to the received term in response to a predetermined repository of medical terms and excludes sentences without a term different to the received term, to provide remaining multiple term sentences. The data processor groups different terms of individual sentences of the multiple term sentences to provide grouped terms, determines whether a medically valid relationship occurs between different terms of an individual group of terms of the grouped terms by using predetermined sentence structure and syntax rules and outputs data representing grouped terms having a medically valid relationship.

16 Claims, 7 Drawing Sheets

(56) References Cited

OTHER PUBLICATIONS

L. Yao, S. Riedel, and A. McCallum, "Collective Cross-Document Relation Extraction Without Labelled Data", In Proceedings of the 2010 Conference on Empirical Methods in Natural Language Processing, pp. 1013-1023. Association for Computational Linguistics, 2010.

Saurav Sahay, et al., "Discovering Semantic Biomedical Relations Utilizing the Web", ACM Trans. Knowledge Discovery. Data, 2:3:1-3:15, Apr. 2008.

Mike Mintz, Steven Bills, Rion Snow, Dan Jurafsky, "Distant Supervision for relation extraction without labeled data", In Proceedings of the Joint Conference of the 47th Annual Meeting of the ACL and the 4th International Joint Conference on Natural Language Processing of the AFNLP: vol. 2-vol. 2, pp. 1003-1011. Association for Computational Linguistics, 2009.

Truc-Vein, T. Nguyen and Alessandro Moschitti, "End-to-End Relation Extraction Using Distant Supervision from External Semantic Repositories", In Proceedings of the 49th Annual Meeting of the Association for Computational Linguistics: Human Language Technologies: short papers—vol. 2, pp. 277-282. Association for Computational Linguistics, 2011.

Y.S. Chang and Dan Roth, "Exploiting Background Knowledge for Relation Extraction", In Proceedings of the 23rd International Conference on Computational Linguistics, pp. 152-160. Association for Computational Linguistics, 2010.

C. Giuliano, A. Lavelli, and L. Romano, "Exploiting shallow linguistic information for relation extraction from biomedical literature", In Proceedings of the Eleventh Conference of the European Chapter of the Association for Computational Linguistics (EACL-2006), pp. 401-408, 2006.

Oana Frunza and Diana Inkpen, "Extraction of Disease-Treatment Semantic Relations from Biomedical Sentences", In Proceeding of the 2010 Workshop on Biomedical Natural Language Processing, pp. 91-98. Association for Computational Linguistics, 2010.

J. Li, Z. Zhang, X. Li, and H. Chen, "Kernel-based learning for biomedical relation extraction", Journal of the American Society for Information Science and TEchnology, 59(5): 756-769, 2008.

Raphael Hoffman, Congle Zhang, Daniel S. Weld, "Learning 5000 Relational Extractors", In Proceedings of the 48th Annual Meeting of the Association for Computational Linguistics, pp. 286-295. Association for Computational Linguistics, 2010.

Philippe Thomas, et al., "Learning to Extraction Protein-Protein Interactions using Distant Supervision", In Proceedings of Workshop on Robust Unsupervised and Semisupervised Methods in Natural Language Processing, pp. 25-32, Hissar, Bulgaria, Sep. 2011.

Chih-Chung Change and Chih-Jen Lin, "A Library for support vector machines", ACM Transactions on Intelligent Systems and Technology, 2:27:1-27:27, 2011. Software available at http://www.csie.ntu.edu.tw/~cjlin/libsvm.

Gyorgy Szarvas and Iryna Gurevych, "TUD: semantic relatedness for relation classification", In Proceedings of the 5th International Workshop on Semantic Evaluation, pp. 2010-213. Association for Computational Linguistics, 2010.

US co-pending patent application titled "A System for Linking Medical Terms for a Medical Knowledge Base" filed on May 24, 2012.

\* cited by examiner

10

SYSTEM FOR GENERATING A MEDICAL KNOWLEDGE BASE

This is a non-provisional application of provisional application Ser. No. 61/533,412 filed on 12 Sep. 2011 and provisional application Ser. No. 61/602,636 filed on 24 Feb. 2012, by S. Somasundaran et al.

FIELD OF THE INVENTION

This invention concerns a system for generating medical knowledge base information by determining whether a medically valid relationship occurs between different terms of grouped terms derived from sentences by using predetermined sentence structure and syntax rules.

BACKGROUND OF THE INVENTION

Medical knowledge bases that capture information about medical entities can be used by reasoning engines and question answering applications to assist medical practitioners. Medical entities are concepts and events such as diseases, treatments, symptoms and drugs, for example. Typical medical knowledge about these entities includes information about their properties, as well as their relationships with other medical concepts. For example, knowledge about a disease includes its symptoms, treatments, complications and drugs that treat it and includes the relation of the disease to entities such as drugs and treatments. Similarly, knowledge about a drug includes its relation to the diseases it treats, its side effects, and its relationship and interactions with other drugs. Thus, relationships between medical entities are needed for constructing comprehensive knowledge bases for them. One way to create knowledge bases is by using a human user encoder to encode his/her knowledge. However, as this process is manually intensive, it is expensive, slow, tedious, and suffers from a lack of wide coverage. A system according to invention principles addresses these deficiencies and related problems.

SUMMARY OF THE INVENTION

A system according to invention principles automatically or partially automatically generates a knowledge base for medical entities based on relationship mining. A system generates medical knowledge base information using a search processor for searching at least one repository of medical information to identify sentences including a received medical term. A data processor searches the identified sentences to identify sentences including a medical term different to the received term in response to a predetermined repository of medical terms and excludes sentences without a term different to the received term, to provide remaining multiple term sentences. The data processor groups different terms of individual sentences of the multiple term sentences to provide grouped terms, determines whether a medically valid relationship occurs between different terms of an individual group of terms of the grouped terms by using predetermined sentence structure and syntax rules and outputs data representing grouped terms having a medically valid relationship.

DETAILED DESCRIPTION OF THE INVENTION

The system advantageously extends a knowledge base and improves its precision and recall. In one embodiment, the system employs large-scale text mining with user human interaction to reduce the time and effort for a human user encoder by automatically extracting relevant knowledge and presenting it to the user for selection. The system automatically discovers medical concepts that are related to a medical entity and determines the type of relationships potentially existing between an entity and discovered entities. This is achieved by mining for knowledge about medical concepts of interest in large (or other) sources of information. In one embodiment, the system automatically searches for an entity (term) in large unstructured databases, retrieves relevant sentences, recognizes other entities in these sentences, and uses knowledge within and outside the sentences to form a hypothesis about the relationship between the given entity and the co-occurring entities. The words "entity" and "term" are used interchangeably herein to indicate a sequence of one or more medical words or text strings. The system creates overall aggregate predictions concerning the relationships for a given entity and presents the predictions to a user (e.g., an expert in the field). The user can either accept or reject system predictions. The system also provides a user with a prediction confidence indicator and additional information discovered via mining in order to assist the user. Thus the system reduces burden on a user whilst facilitating improved medical knowledge base coverage and precision.

Figure 1:
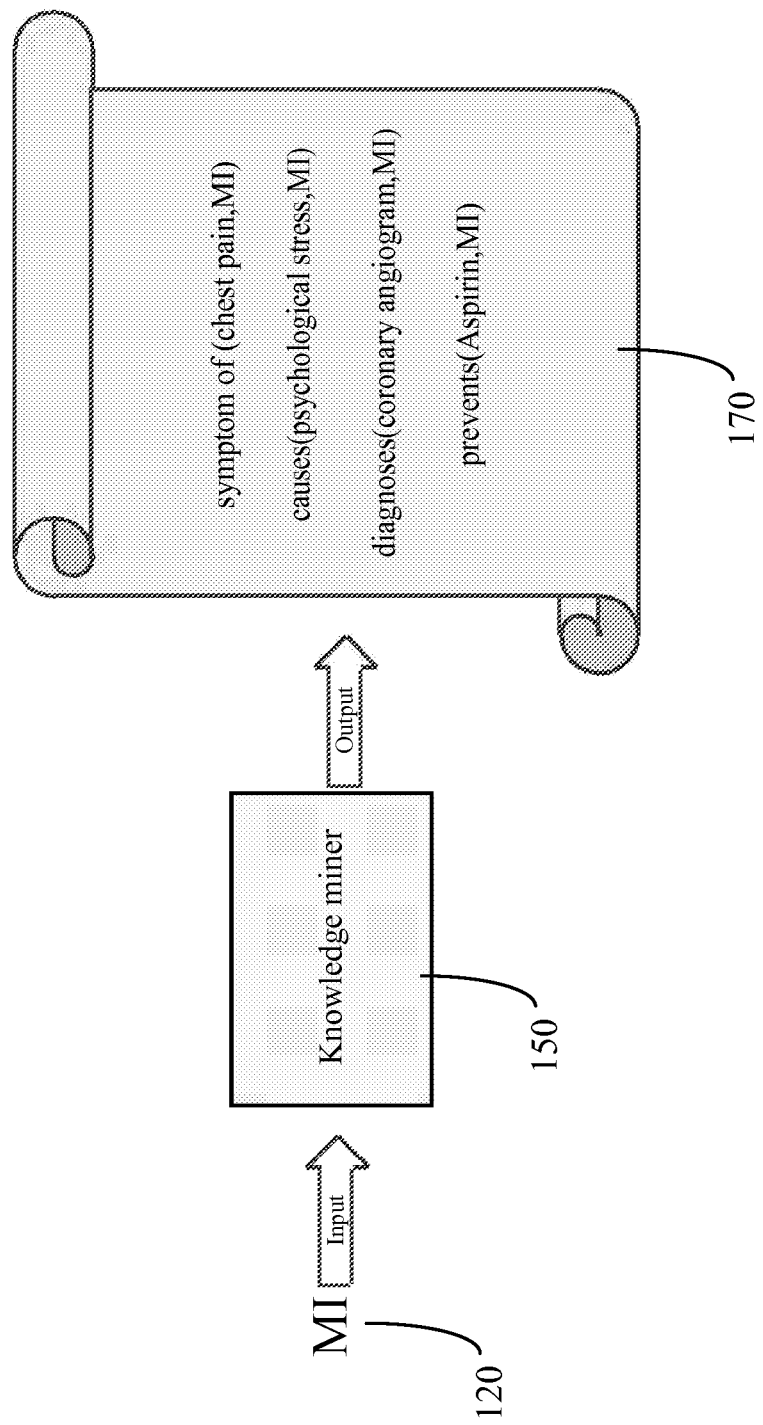
FIG. 1 shows a function overview of a system for generating medical knowledge base information, according to an embodiment of the invention.

FIG. 1 shows a function overview of a system for generating medical knowledge base information. The system automatically mines large datasets to discover other entities that co-occur with a particular entity (that is, that occur in the same sentence as this entity) and uses different classifiers to establish relationships between the particular entity and the discovered entities. In other embodiments, the system automatically mines large datasets to discover other entities that co-occur, i.e., that occur together in other text segments such as sentence portions, paragraphs, pages, for example. Input (120) to medical knowledge base information generation system 150 comprises data indicating an entity (here MI, Myocardial Infarction) for which knowledge is to be built. The output 170 of the system comprises a list of tuples (term pairs) encoding information concerning input 120. A tuple is represented as relation(entity1, entity2), where entity1 (or entity2) is the entity of interest, and corresponding entity2 (or entity1) is an entity discovered by the system, and relation describes the manner in which the two are related. The list of tuples is presented to a user for review, rejection or acceptance and in response to acceptance, addition to a knowledge base. Myocardial Infarction (MI) data 120 (representing a disease), is input to Knowledge miner unit 150. Output 170 is a tuple list. System 150 determines chest pain is a symptom of MI (tuple: symptom of (chest pain, MI)), psychological stress is a cause of MI (tuple: causes(psychological stress, MI)), coronary angiogram diagnoses MI (tuple: diagnoses(coronary angiogram, MI)) and Aspirin prevents MI (tuple: prevents(Aspirin, MI)).

Figure 2:
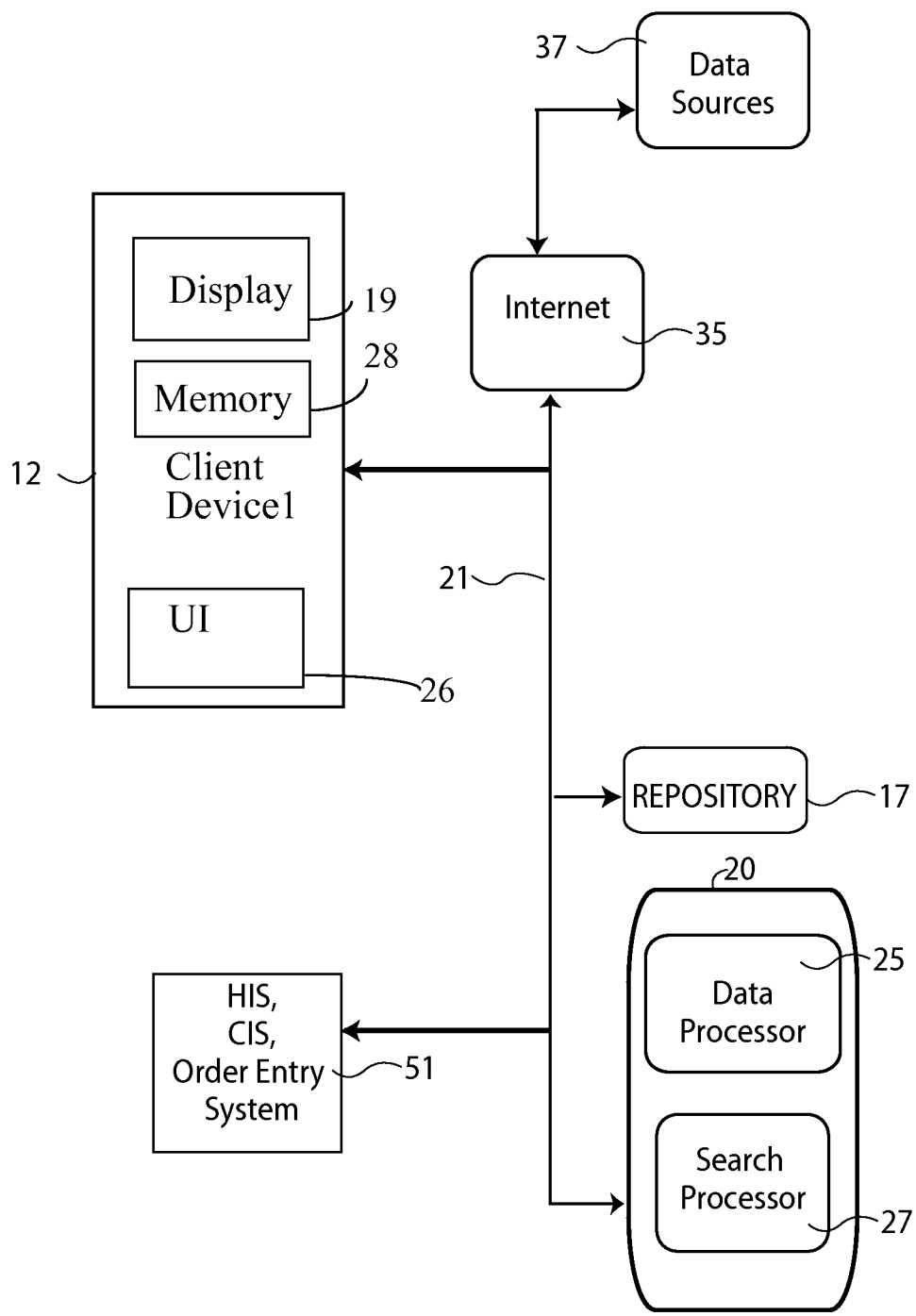
FIG. 2 shows a system for generating medical knowledge base information, according to an embodiment of the invention.

FIG. 2 shows system 10 for generating medical knowledge base information. System 10 includes one or more processing devices on network 21 (e.g., workstations, computers or portable devices such as notebooks, Personal Digital Assistants, phones) 12 that individually include a user interface 26 enabling user interaction with a Graphical User Interface (GUI) and display 19 supporting GUI and medical data, image and administrative information presentation in response to predetermined user (e.g., physician, nurse administrator) specific preferences. System 10 also includes at least one repository 17, server 20 and HIS 51 (including ADT, clinical information, order entry and other applications) intercommunicating via network 21. Server 20 includes data processor 25 and search processor 27. Server 20 communicates via network 21 and Internet 35 (or via Internet 35 directly, connection not shown to preserve drawing clarity) with data sources 37. At least one repository 17 comprises information including patient medical record data, hospital transaction message data, medical treatment information, medical texts and guidelines and user preferences, a predetermined repository of medical terms, predetermined semantic information in one or more different repositories used to identify a medical relationship in response to meaning and definition of a first and different second term and predetermined sentence structure and syntax rules, for example.

Search processor 27 searches at least one repository 17 of medical information to identify sentences including a received medical term. Data processor 25 searches the identified sentences to identify sentences including a medical term different to the received term in response to a predetermined repository of medical terms and excludes sentences without a term different to the received term, to provide remaining multiple term sentences. Data processor 25 groups different terms of individual sentences of the multiple term sentences to provide grouped terms (e.g. tuples or pairs) and determines whether a medically valid relationship occurs between different terms of an individual group of terms of the grouped terms by using predetermined sentence structure and syntax rules. Processor 25 outputs data representing grouped terms having a medically valid relationship.

Figure 3:
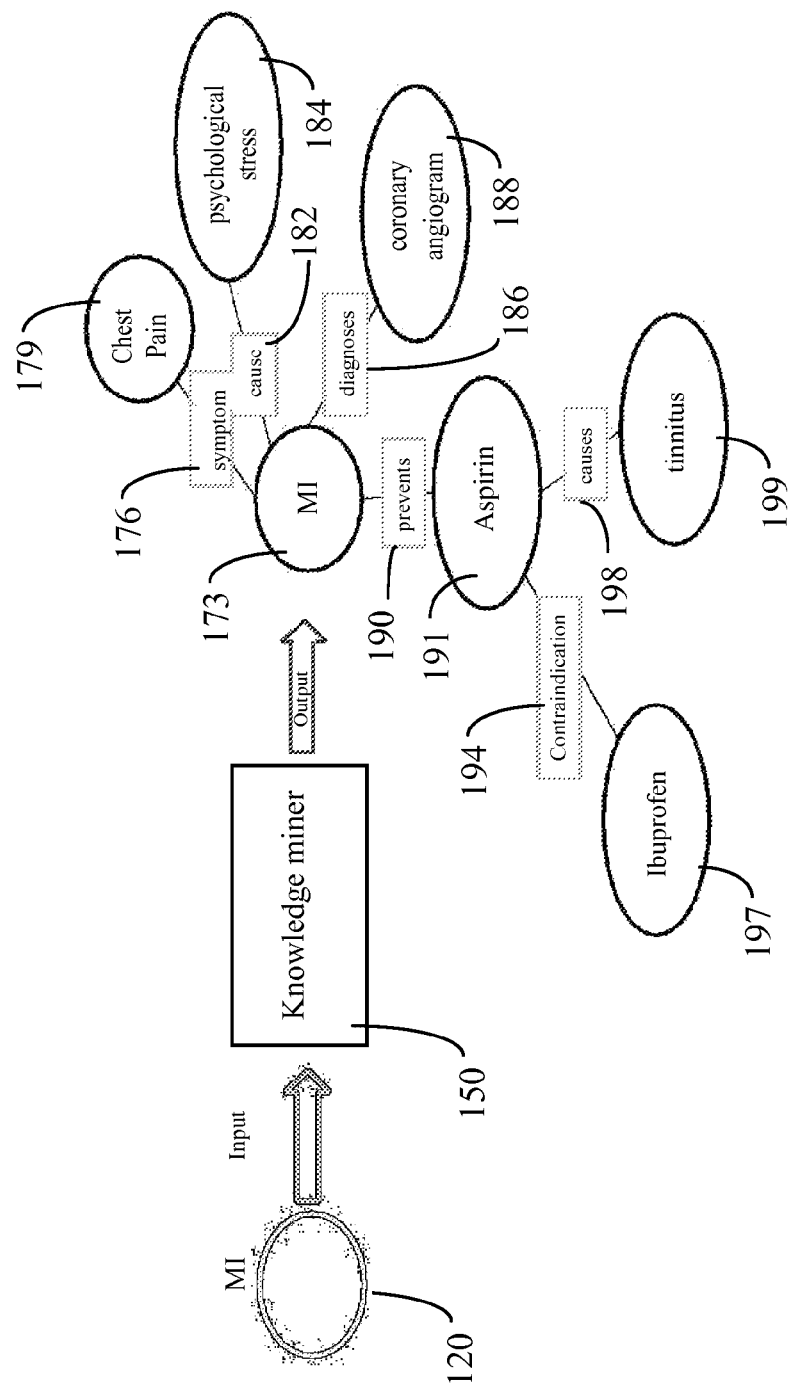
FIG. 3 shows functions of a system for generating medical knowledge base information, according to an embodiment of the invention.

FIG. 3 shows functions of a system for generating medical knowledge base information and representing knowledge generated by the system as a plot of medical entities that are connected to one another via their respective relationships. Entities comprise nodes MI 173, chest pain 179, psychological stress 184 and coronary angiogram 188 and the links are tuples relating the nodes. The relationships corresponding to the tuples comprise symptom 176, cause 182 and diagnosis 186. In a similar manner to FIG. 1, input data 120 identifying MI is processed by system 150 for generating medical knowledge base information to provide output information about MI comprising nodes 173, 179, 184 and 188, and tuples 176, 182 and 186. In a separate analysis with data identifying Aspirin as input, system 150 discovers that Aspirin 191 prevents 190 MI as a contraindication 194 for Ibuprofen 197, and it can cause 198 tinnitus 199. The overlapping plot (prevents (Aspirin, MI)) discovered from the subsequent separate analysis is merged to provide the knowledge plot shown in FIG. 3.

Figure 4:
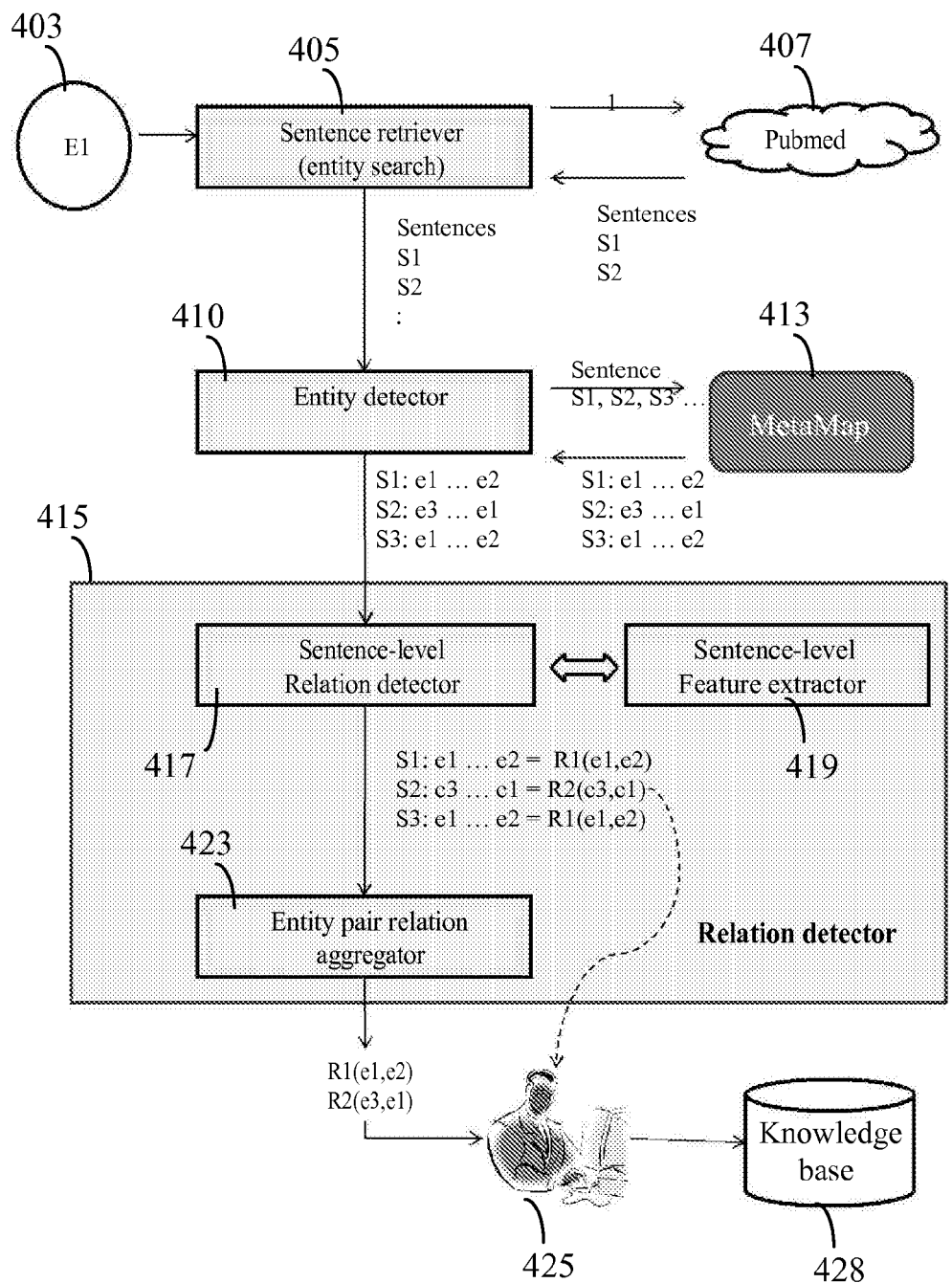
FIG. 4 shows a system and process flow for generating medical knowledge base information using intra-sentence term relationship detection, according to an embodiment of the invention.

FIG. 4 shows a system and process flow for generating medical knowledge base information using intra-sentence term relationship detection. Sentence retrieval unit 405 comprises a search and retrieval module. Unit 405 receives data representing an entity 403 (e.g., the term Myocardial Infarction) and queries text available at an Internet data source 407 (e.g. Pubmed) for sentences containing this entity. Unit 405 provides output data comprising a set of sentences containing entity 403 (e.g. "Reduction of early ventricular arrhythmia by acebutolol in patients with acute myocardial infarction") to entity detector 410. Entity detector 410 detects a portion or preferably all medical entities present in an input sentence received from unit 405. Medical entity identifiers such as MetaMap 413 are used in one embodiment to identify medical entities. MetaMap is a system used in biomedical entity identification and is provided by the National Library of Medicine (NLM). In addition to identifying entities in the sentence, MetaMap also maps an identified entity to a unique Unified Medical Language System (UMLS) concept which attaches semantic information to an entity annotation. For example, in response to MetaMap 413 being presented with the sentence "Reduction of early ventricular arrhythmia by acebutolol in patients with acute myocardial infarction", MetaMap 413 outputs the following entities, Reduction, ventricular arrhythmia, acebutolol and acute myocardial infarction.

Unit 410 pairs entities found within a sentence to form an entity pair, since as these entities occur in the same sentence, it is likely that they are related to one another. The entity pairs are provided to relation detector 415. In the example, the entity pairs created by unit 410 are:
Reduction, ventricular arrhythmia
Reduction, acebutolol
Reduction, acute myocardial infarction
ventricular arrhythmia, acebutolol
ventricular arrhythmia, acute myocardial infarction
acebutolol, acute myocardial infarction Relation detector 415 employs different embodiments. In one embodiment, relation detector 415 determines if entities in each entity pair provided by unit 410 have a valid medical relationship, or if they are unrelated. Sentences that do not contain one or more entities in addition to the original entity are filtered out at this stage. In one embodiment, to determine if an entity pair is related unit 415 identifies where two entities of an individual entity pair co-occur in a sentence and classifies the relationship expressed between the individual entity pair in that sentence. Relationships between entities are established by predicting the relationship for several instances (sentences in which the entity pair occur), and by aggregating the individual predictions. The greater the number of sentences for which a particular relationship is detected, the greater the likelihood that the entities are related via a particular relationship.

Sentence-level Relation Detector 417 employs feature extractor 419 using linguistic clues, such as the structure of a sentence, syntax and sentence-level semantics to find an entity pair relationship for an individual sentence. Syntax comprises the rules that govern the ways words combine to form phrases, clauses, and sentences and the arrangement of words in a sentence and semantics comprises language meaning. For example, unit 417 processes the sentence "Reduction of early ventricular arrhythmia by acebutolol in patients with acute myocardial infarction" and the entity pair <ventricular arrhythmia, acebutolol>, using linguistic clues, including structure of a sentence, syntax and sentence-level semantics to detect a reduces relationship (reduces(acebutolol,ventricular arrhythmia)), and determines that there is no relationship for the pair <Reduction, acute myocardial infarction>. In one embodiment unit 417 identifies a relationship using a lookup table associating a particular relationship with predetermined terms.

In response to identification of relationships between pairs of entities and classification of entities in input sentences, Entity Pair Relation Aggregator 423 creates a cumulative score of each relationship type detected between different pairs of different entities. In one embodiment the score comprises a simple majority class selector. For example, if unit 417 processes 10 sentences containing both MI and Aspirin, and the sentence relationship detector 417 predicts a prevents relation in 60% of the sentences, and a diagnoses relationship in only 30% of the sentences, a majority class aggregator selects the prevents relation for the entity pair (prevents(Aspirin, MI)). In another embodiment, unit 417 uses a more detailed weighting scheme to predict and select a relationship based on the number of instances encountered for an entity pair. Unit 423 presents predicted relationship tuples to a user along with associated sentences containing the entity pairs. This facilitates user 425 judgment and selection of entity pairs to be incorporated in knowledge base 428, especially in the case of new and rare entities.

Figure 5:
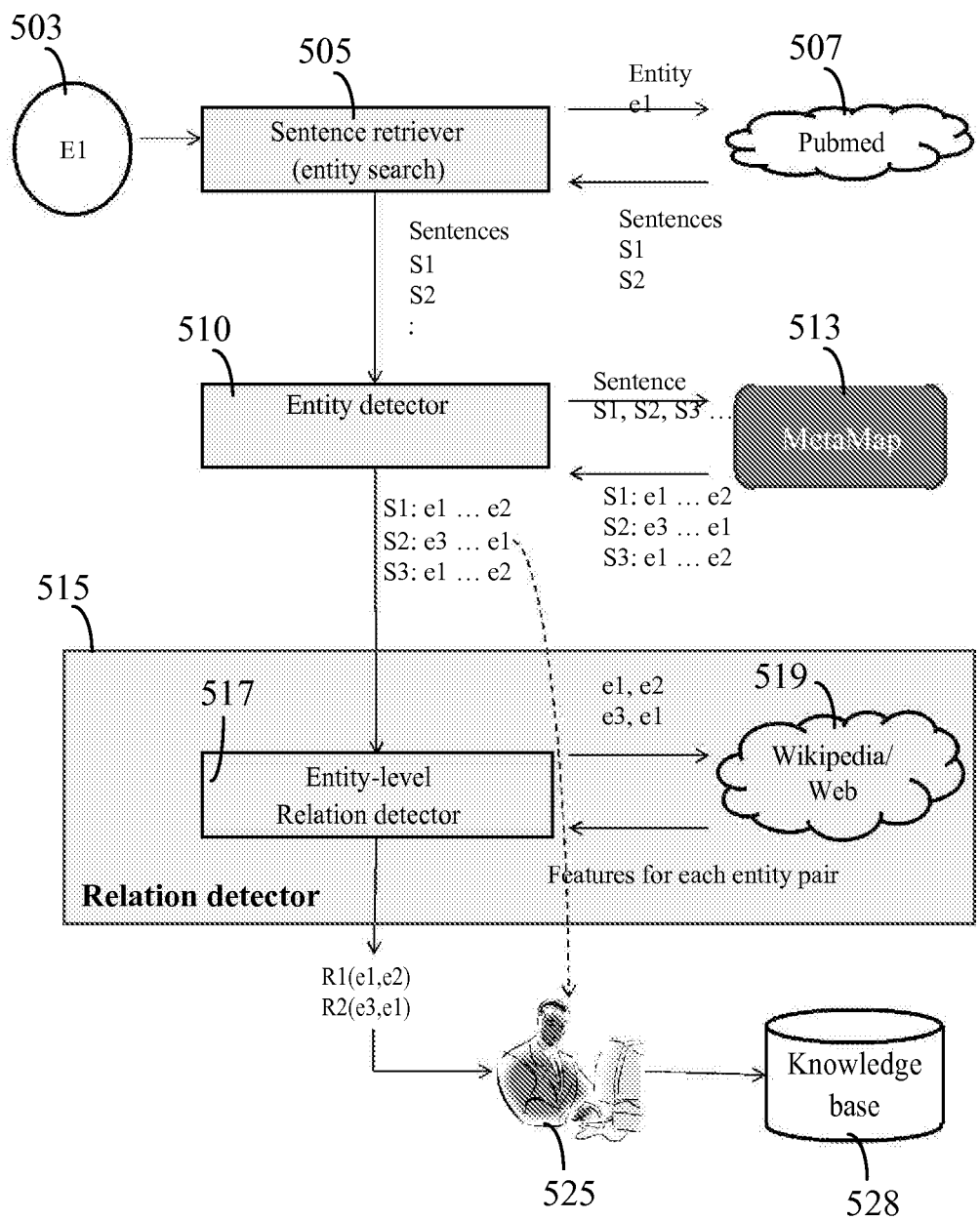
FIG. 5 shows a system and process flow for generating medical knowledge base information using semantic based term relationship detection, according to an embodiment of the invention.

FIG. 5 shows a system and process flow for generating medical knowledge base information using semantic based term relationship detection. Sentence retrieval unit 505 comprises a search and retrieval module. Unit 505 receives data representing an entity 503 and queries text available at an Internet data source 507 (e.g. Pubmed) for sentences containing this entity. Unit 505 provides output data comprising a set of sentences containing entity 503 to entity detector 510. Entity detector 510 detects a portion or preferably all medical entities present in an input sentence received from unit 505. Medical entity identifiers such as MetaMap 513 are used in one embodiment to identify medical entities. Unit 510 pairs entities found within a sentence to form an entity pair, since as these entities occur in the same sentence, it is likely that they are related to one another. The entity pairs are provided to relation detector 515.

Relation detector 515 determines if entities in each entity pair provided by unit 510 have a valid medical relationship, or if they are unrelated. Sentences that do not contain one or more entities in addition to the original entity are filtered out at this stage. In this embodiment, to determine if an entity pair is related, entity-level classifier 517 identifies where two entities of an individual entity pair co-occur in a sentence and classifies the relationship expressed between the individual entity pair in that sentence. Unit 517 detects a relationship between entities using properties of the entities themselves to train a classifier (such as a neural network) to detect the relationship between the entities. Unit 517 retrieves semantic information regarding each of the entities from different web resources 519, for example. Entity-level classifier 517 uses this information for detecting a relationship in a single step (that is, without aggregation of entity relationship type data). For example, in order to determine a relationship between Aspirin and MI, unit 517 looks up medical texts and online resources (e.g. Wikipedia) 519 for information about Aspirin (such as its drug category and other properties) and MI (e.g. its disease category) and uses the information for inferring a relationship. In response to identification of relationships between pairs of entities, unit 525 presents relationship tuples to a user along with associated sentences containing the entity pairs. This facilitates user 525 judgment and selection of entity pairs to be incorporated in knowledge base 528, especially in the case of new and rare entities.

System 10 in one embodiment provides semi-automatic construction of knowledge bases by combining large-scale text mining and user interaction. The input to the system is a set of entities that a user is interested in. The output of the system is in the form of tuples representing relationships between the entities. A user reviews the displayed tuples and associated sentences and accepts or rejects system predicted relationships. The system also provides additional support sentences that contain the entity pair concerned. The information gathered by the system is also presented by system 10 in the form of an entity network that can be used to represent and navigate a knowledge space. This network can be used by graph methods and reasoning engines to create inferences. While the system primarily assists in the creation of medical knowledge bases, it may also be employed in other domains where there is a need for capturing knowledge.

Figure 6:
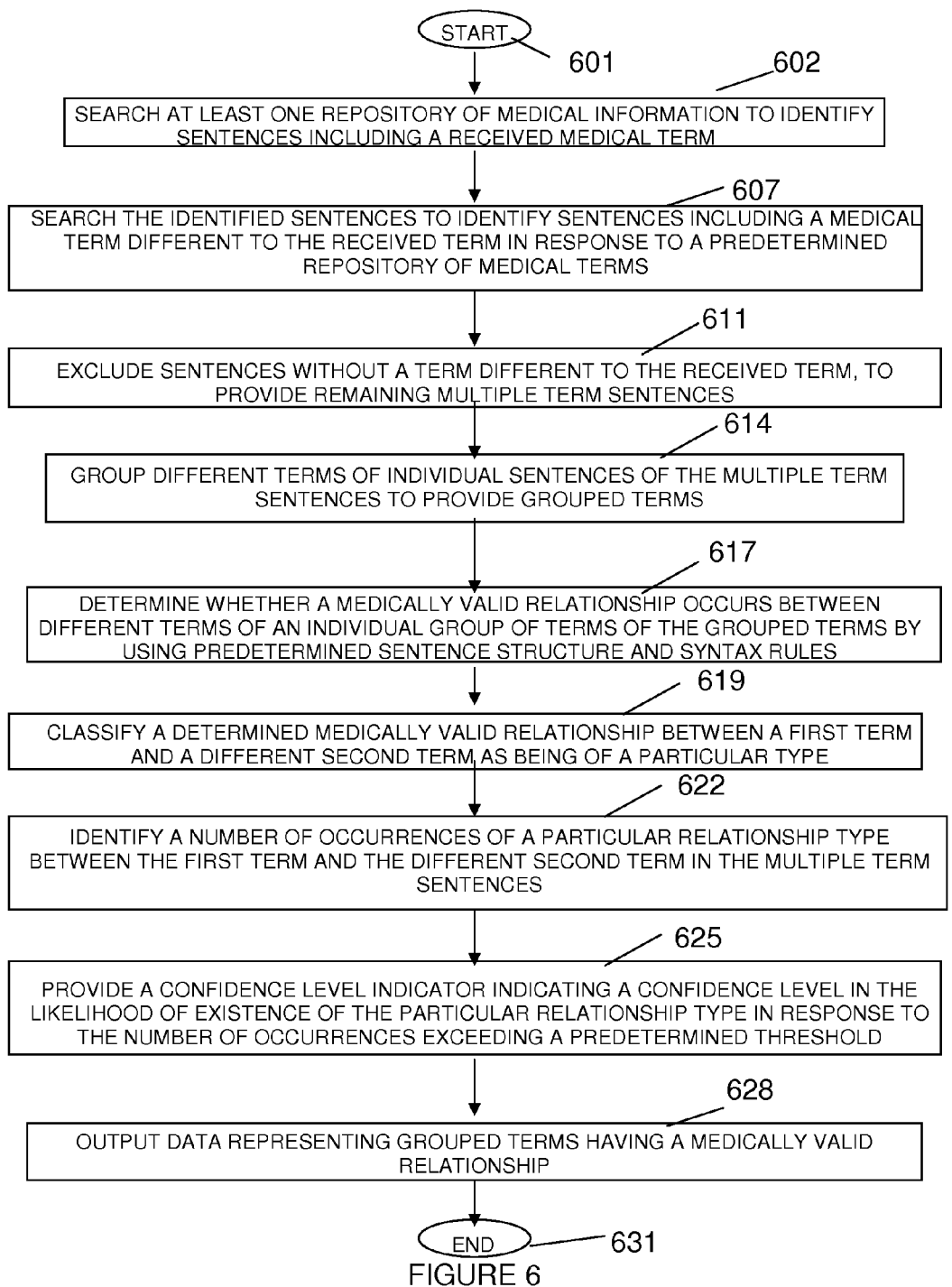
FIG. 6 shows a flowchart of a process performed by a system for generating medical knowledge base information using a first embodiment relationship detector, according to an embodiment of the invention.

FIG. 6 shows a flowchart of a process performed by system 10 (FIG. 2) for generating medical knowledge base information. In step 602 following the start at step 601, search processor 27 searches at least one repository 17 of medical information to identify sentences including a received medical term. In step 607, data processor 25 searches the identified sentences to identify sentences including a medical term different to the received term in response to a predetermined repository of medical terms. Processor 25 in step 611 excludes sentences without a term different to the received term, to provide remaining multiple term sentences and in step 614 processor 25 groups different terms of individual sentences of the multiple term sentences to provide grouped terms comprising determining all pairs of different terms of an individual sentence and a group of terms comprises a pair of terms. In step 617 processor 25 determines whether a medically valid relationship occurs between different terms of an individual group of terms of the grouped terms by using predetermined sentence structure, syntax rules and predetermined sentence structure and semantics rules and by determining a verb links the first and different second terms. Processor 25 further includes text representing the relationship in the grouped terms Data processor 25 in step 619, classifies a determined medically valid relationship between a first term and a different second term as being of a particular type and in step 622 identifies a number of occurrences of a particular relationship type between the first term and the different second term in the multiple term sentences. In step 625 processor 25 provides a confidence level indicator indicating a confidence level in the likelihood of existence of the particular relationship type in response to the number of occurrences exceeding a predetermined threshold. Processor 25 predicts likelihood of existence of the particular relationship type in response to the number of occurrences exceeding a predetermined threshold. In one embodiment, processor 25 predicts a likelihood of existence of the particular relationship type in response to a weighted combination of different types of sentence structural relationship identified between the first term and the different second term. In another embodiment, processor 25 predicts a likelihood of existence of the particular relationship type in response to different types of sentence structural relationship identified between the first term and the different second term and different types of semantic relationship identified between the first term and the different second term. In step 628, processor 25 outputs data representing grouped terms having a medically valid relationship. The process of FIG. 6 terminates at step 631.

Figure 7:
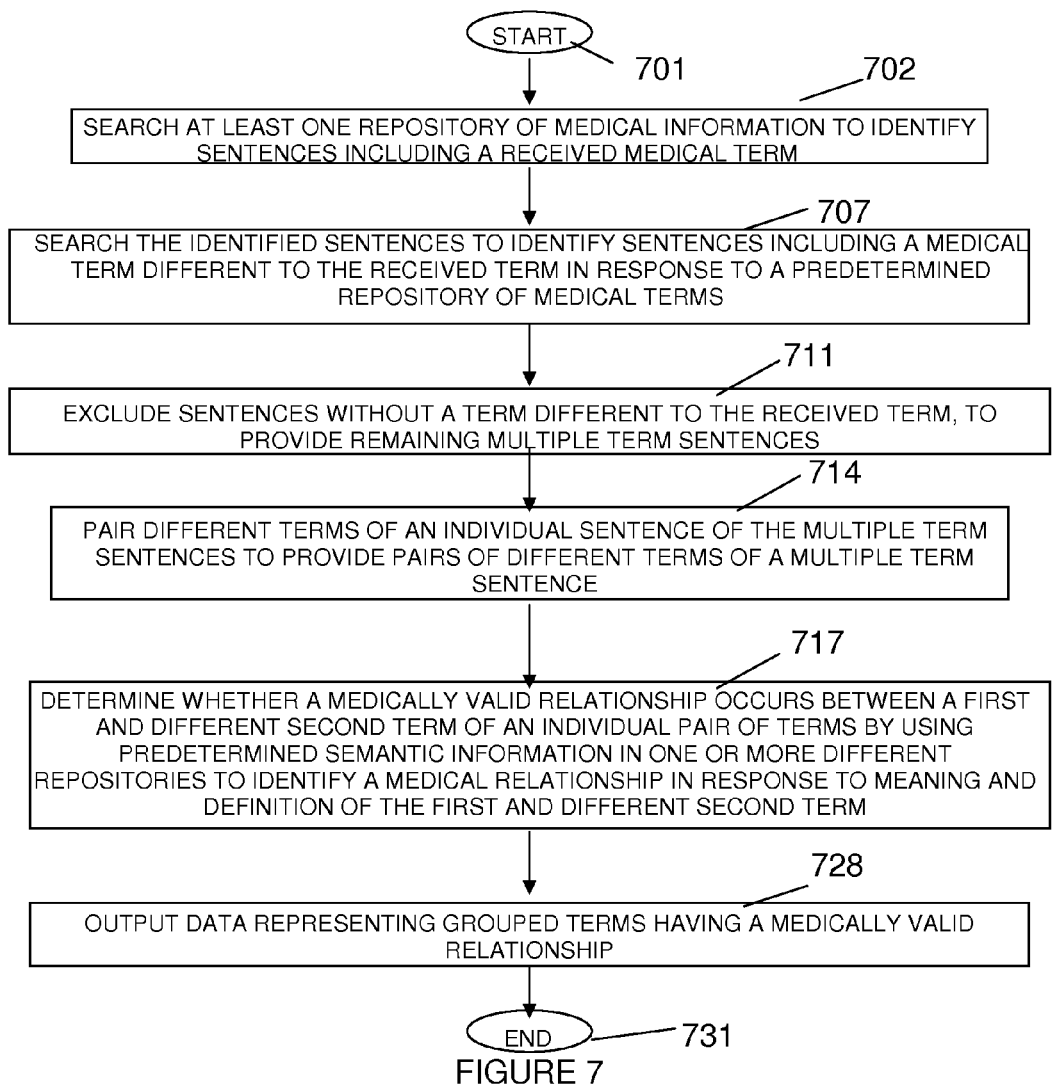
FIG. 7 shows a flowchart of a process performed by a system for generating medical knowledge base information using a second embodiment relationship detector, according to an embodiment of the invention.

FIG. 7 shows a flowchart of a process performed by system 10 (FIG. 2) for generating medical knowledge base information using a second embodiment relationship detector. In step 702 following the start at step 701, search processor 27 searches at least one repository 17 of medical information to identify sentences including a received medical term. In step 707, data processor 25 searches the identified sentences to identify sentences including a medical term different to the received term in response to a predetermined repository of medical terms. Processor 25 in step 711 excludes sentences without a term different to the received term, to provide remaining multiple term sentences and in step 714 pairs different terms of individual sentences of a multiple term sentence to provide pairs of different terms of a multiple term sentence. In step 717, processor 25 determines whether a medically valid relationship occurs between a first and different second term of an individual pair of terms by using predetermined semantic information in one or more different repositories to identify a medical relationship in response to meaning and definition of the first and different second term. In step 728, processor 25 outputs data representing grouped terms having a medically valid relationship. The process of FIG. 7 terminates at step 731.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system generates a knowledge base for medical terms by automatically searching for terms in databases, retrieves relevant sentences, recognizes other terms in these sentences, and uses knowledge within and outside the sentences to form a hypothesis about the relationship between individual terms within a sentence. Further, the processes and applications may, in alternative embodiments, be located on one or more (e.g., distributed) processing devices on a network linking the units of FIG. 1. Any of the functions and steps provided in FIGS. 1-7 may be implemented in hardware, software or a combination of both. No claim element herein is to be construed under the provisions of 35 U.S.C. 112, sixth paragraph, unless the element is expressly recited using the phrase "means for."

What is claimed is:

1. A system for generating medical knowledge base information, comprising:
    a non-transitory computer readable medium for storing computer readable instructions;
    a search processor device operative with the computer readable instructions to search at least one repository of medical information to identify sentences including a received medical term; and
    a data processor device operative with the computer readable instructions to perform steps including,
        searching the identified sentences to identify sentences including a medical term different to the received term in response to a predetermined repository of medical terms,
        excluding sentences without a term different to the received term, to provide remaining multiple term sentences, grouping different terms of individual sentences of said multiple term sentences to provide grouped terms, determining whether a medically valid relationship occurs between different terms of an individual group of terms of said grouped terms by using predetermined sentence structure and syntax rules, and outputting data representing grouped terms having a medically valid relationship.

2. A system according to claim 1, wherein
said data processor device is further operative with the computer readable instructions to determine whether a medically valid relationship occurs between different terms of said individual group of terms using predetermined sentence structure and semantics rules and includes text representing said relationship in said grouped terms.

3. A system according to claim 1, wherein
said data processor device is further operative with the computer readable instructions to,
classify a determined medically valid relationship between a first term and a different second term as being of a particular type,
identify a number of occurrences of a particular relationship type between said first term and said different second term in said multiple term sentences.

4. A system according to claim 3, wherein
said data processor device is further operative with the computer readable instructions to predict likelihood of existence of said particular relationship type in response to said number of occurrences.

5. A system according to claim 4, wherein
said data processor device is further operative with the computer readable instructions to predict said likelihood of existence of said particular relationship type in response to said number of occurrences exceeding a predetermined threshold.

6. A system according to claim 4, wherein
said data processor device is further operative with the computer readable instructions to provide a confidence level indicator indicating a confidence level in said likelihood of existence of said particular relationship type in response to said number of occurrences exceeding a predetermined threshold.

7. A system according to claim 4, wherein
said data processor device is further operative with the computer readable instructions to predict a likelihood of existence of said particular relationship type in response to a weighted combination of different types of sentence structural relationship identified between said first term and said different second term.

8. A system according to claim 4, wherein
said data processor device is further operative with the computer readable instructions to predict a likelihood of existence of said particular relationship type in response to different types of sentence structural relationship identified between said first term and said different second term.

9. A system according to claim 4, wherein
said data processor device is further operative with the computer readable instructions to predict a likelihood of existence of said particular relationship type in response to different types of semantic relationship identified between said first term and said different second term.

10. A system according to claim 1, wherein said grouping different terms comprises pairing different terms.

11. A system according to claim 1, wherein said grouping different terms of an individual sentence comprises determining all pairs of different terms of an individual sentence and a group of terms comprises a pair of terms.

12. A system according to claim 1, wherein
said data processor device is further operative with the computer readable instructions to determine whether a medically valid relationship occurs between first and different second terms of an individual group of terms of said grouped terms by determining a verb that links the first and different second terms.

13. A system for generating medical knowledge base information, comprising:
a non-transitory computer readable medium for storing computer readable instructions;
a search processor device operative with the computer readable instructions to search at least one repository of medical information to identify sentences including a received medical term; and
a data processor device operative with the computer readable instructions to perform steps including,
searching the identified sentences to identify sentences including a medical term different to the received term in response to a predetermined repository of medical terms,
excluding sentences without a term different to the received term, to provide remaining multiple term sentences,
pairing different terms of an individual sentence of said multiple term sentences to provide pairs of different terms of a multiple term sentence,
determining whether a medically valid relationship occurs between different terms of an individual pair of terms by using predetermined sentence structure and syntax rules, and
outputting data representing paired terms having a medically valid relationship.

14. A system according to claim 13, wherein
said data processor device is further operative with the computer readable instructions to pair different terms of an individual sentence of said multiple term sentences to provide all pairs of different terms of a multiple term sentence.

15. A system for generating medical knowledge base information, comprising:
a non-transitory computer readable medium for storing computer readable instructions;
a search processor device operative with the computer readable instructions to search at least one repository of medical information to identify sentences including a received medical term; and
a data processor device operative with the computer readable instructions to perform steps including,
searching the identified sentences to identify sentences including a medical term different to the received term in response to a predetermined repository of medical terms,
excluding sentences without a term different to the received term, to provide remaining multiple term sentences,
pairing different terms of an individual sentence of said multiple term sentences to provide pairs of different terms of a multiple term sentence,
determining whether a medically valid relationship occurs between a first term and different second term of an individual pair of terms by using predetermined semantic information in one or more different repositories to identify a medical relationship in response to meaning and definition of said first and different second term, and outputting data representing paired terms having a medically valid relationship.

16. A method for generating medical knowledge base information, comprising the steps of:

searching at least one repository of medical information to identify sentences including a received medical term;

searching the identified sentences to identify sentences including a medical term different to the received term in response to a predetermined repository of medical terms;

excluding sentences without a term different to the received term, to provide remaining multiple term sentences;

grouping different terms of individual sentences of said multiple term sentences to provide grouped terms;

determining whether a medically valid relationship occurs between different terms of an individual group of terms of said grouped terms by using predetermined sentence structure and syntax rules; and outputting data representing grouped terms having a medically valid relationship.

* * * * *